United States Patent [19]

Snyder

[11] Patent Number: 5,108,385

[45] Date of Patent: Apr. 28, 1992

[54] DIAPER WITH DISPOSABLE INSERT AND REUSABLE COVER

[76] Inventor: William D. Snyder, 151 N.E. 173rd St., North Miami, Fla. 33162

[21] Appl. No.: 555,900

[22] Filed: Jul. 19, 1990

[51] Int. Cl.⁵ ............................................. B32B 31/04
[52] U.S. Cl. ............................................. 604/397
[58] Field of Search ............... 604/358, 383, 378, 377, 604/385.1, 385.2, 391, 393, 397, 398, 361

[56] References Cited

U.S. PATENT DOCUMENTS

| | | | |
|---|---|---|---|
| 3,039,466 | 6/1962 | Wilson | 604/398 |
| 4,753,643 | 6/1988 | Kassai | 604/359 |
| 4,892,598 | 1/1990 | Stevens et al. | 604/339 X |

Primary Examiner—David Isabella
Attorney, Agent, or Firm—Malin, Haley, McHale, DiMaggio & Crosby

[57] ABSTRACT

A diaper having a disposable insert and a reusable cover is provided. The insert is held in place relative to the cover by a hook and loop closure system operating through apertures extending through the insert. The insert may include a liquid absorbant layer. The inserts may be provided attached end to end by a perforated connection to facilitate tearing and consequent separation of the inserts. In addition the inserts may be stacked to provide easy access. A design may be applied to the outside of the resuable cover.

12 Claims, 3 Drawing Sheets

DIAPER WITH DISPOSABLE INSERT AND REUSABLE COVER

BACKGROUND OF THE INVENTION

1. Field of the Invention

This device relates to diapers and more particularly to diapers having disposable inserts and reusable insert covers.

2. Related Art

Diapers containing inserts are well known in the art. For example, the following U.S. issued patents show diapers with removable inserts:

U.S. Pat. No. 4,018,226, issued to Korgemets, Apr. 9, 1977,
U.S. Pat. No. 4,036,234, issued to Ishizuka, Jul. 19, 1977,
U.S. Pat. No. 4,072,150, issued to Glassman, Feb. 7, 1978, and,
U.S. Pat. No. 4,596,568, issued to Flug, Jun. 24, 1986.

In these patented devices, the removable insert is attached to the outer cover by means such as sewing, use of a rupturable adhesive, or by placing the cover within specially designed flaps. No prior art device teaches or suggests positioning and maintaining the cover relative to the outer cover by easily removable means disposed through the body of the liner.

SUMMARY OF THE INVENTION

A diaper is provided having two parts, a disposable inner liner and a reusable outer cover. The disposable inner liner comprises an absorbent material and may include a wick-type covering to draw any contaminant from a wearer and direct it to the absorbent material. In the preferred embodiment, the disposable inner liner also has a liquid impervious surface on the side of the disposable inner liner not in contact with the baby.

The reusable outer cover may be constructed of a variety of materials including cotton and may have an outer layer or shell which is impervious to liquids. The reusable outer cover is formed in the traditional hourglass shape. Arranged along opposite side edges of the outer cover are flaps. The flaps are attached to the outer cover along fold lines and are formed, in the preferred embodiment, during manufacture. Spaced along either side of the fold lines are patches of hook and loop fastening material such as that sold under the trademark VELCRO. The hook and loop material is arranged on the inner or body-facing side of the outer cover so that patches connected to the flap portion are of male hook and loop material and the corresponding patches on the outer cover are of the female hook and loop material, or vice versa, so that folding the flaps about the fold lines and bringing the male VELCRO patches into contact with the female VELCRO patches produces fastening of the flaps to the outer cover. The side edges of the inner liner are adapted to overlay the hook and loop patches which are connected to the outer cover, and define windows or apertures therein through which the respective male and female hook and loop patches are mated. Thus, when the inner liner is laid on the body-facing surface of the outer cover, the hook and loop patches of the outer cover align with the apertures of the inner liner. The patches of the outer cover are thereby exposed through the apertures of the inner liner. The flaps may then be folded over onto the outer cover so that the appropriate hook or loop patches on the flaps may intermesh and connect with the corresponding respective loop or hook patches of the outer cover. In this way, the inner liner is securely held in position relative to the outer cover.

After it becomes necessary to remove and dispose of the inner liner, the flaps are removed from their sealing connection with the outer cover through the hook and loop patches. At this time the inner layer may be removed and disposed of. A new inner layer may then be placed upon the outer cover where it may be attached as described above.

Because the inner liner contains any contaminant the outer cover is unsoiled and available to be reused with a new inner liner. The outer cover may be used many times while the inner liners are used and disposed of as necessary. Inner liners may be provided in an end-to-end roll assembly such as is common for paper towels, so that an inner liner may be removed from the roll along a perforation. In this way, a user need only buy a single outer cover and a roll of inner liners.

The outer cover may also have a series of strips of elastic material sewn in the area corresponding to the leg of the diaper to create a snug fit around the baby's legs. In addition, elastic material may be sewn into the waist band to further aid in fitting the baby. The front and back portions of the outer cover may be attached to each other in the familiar diaper configuration by any sealing method. However, in the preferred embodiment, this sealing is achieved by the use of hook and loop closures where tabs on the back waistband and on the outer surface of the flaps of the outer cover corresponding to the rear portion of the outer cover contain either hooks or loops which are attached to corresponding respective loops or hooks on pads on the front waistband of the diaper and on the outer surface of the flaps of the outer cover corresponding to the front portion of the outer cover, respectively.

It is therefore an object of this invention to provide a diaper which reduces the amount of non-degradable refuse produced by each change of diaper.

It is another object of the invention to provide a diaper with a disposable insert and reusable cover that easily positions and secures the disposable insert relative to the reusable cover.

It is another object of the invention to provide a practical diaper with a disposable insert and reusable cover whereby many disposable inserts are readily available to be used with the reusable cover.

It is further an object of the invention to provide a diaper whose cost per change of diaper is less than the cost per change of an ordinary disposable diaper due to the lower cost of a disposable insert relative to the cost of an entire ordinary disposable diaper.

It is still further an object of the invention to provide a diaper upon which a design may easily be placed.

Having now briefly described the instant invention, reference will be had to a detailed description including reference to drawings, wherein common elements are referred to by identical numbers.

DETAILED DESCRIPTION OF THE INVENTION

Figure 1:
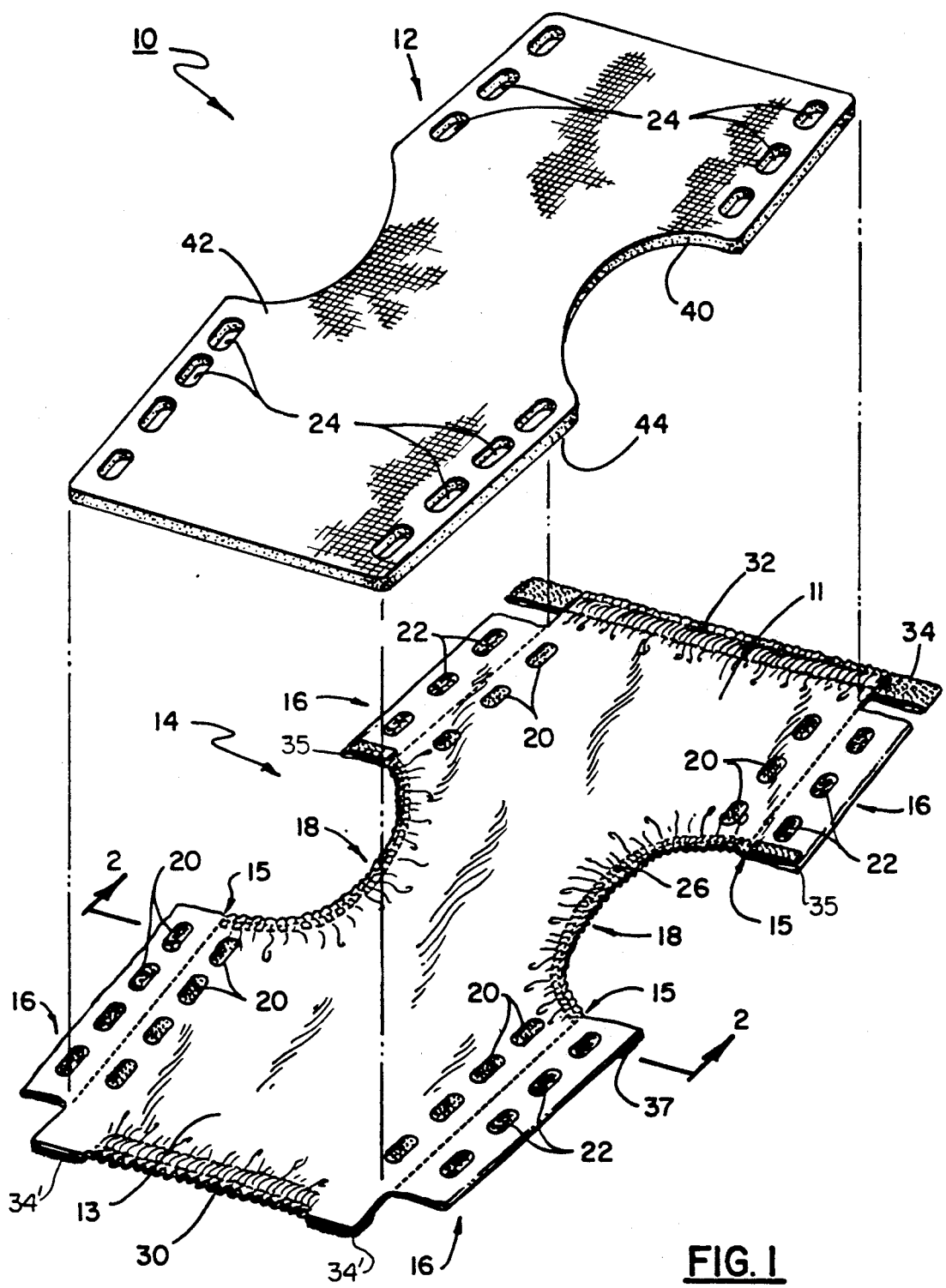
FIG. 1 is a perspective view of the invention showing a disposable inner liner positioned above an open outer cover.

The outer cover 14 of the diaper 10 is shown in an open position in FIG. 1. The outer cover 14 has basically an hourglass shape with a rear portion 11 and a front portion 13. Leg indentations 18 are provided to allow placement of the baby's legs therein. Leg indentations 18 may have elastic material 26 sewn into them to form a tight seal around the baby when diaper 10 is worn.

Flaps 16 are integrally attached in the preferred embodiment along side edges of outer cover 14 along fold lines 15 as shown.

Symmetrically arranged on either side of fold lines 15 are connecting means such as hook and loop patches 20 and 22 on outer cover 14 and flap 16, respectively. Patches 20 and 22 may be formed as elongated ovals or any desired shape. Cover patches 20 are comprised of male hook material while the corresponding flap patches 22 are comprised of female loop material, or vice versa. Patches 20, 22 are attached to the outer cover 14 and flaps 16 respectively by any common means, so as to be held securely in place on their respective structures.

Outer cover 14 also has a front waistband 30 and a rear waistband 32. Front and rear waistbands 30, 32 may include elastic material sewn therein to aid in fitting around the wearer. Also provided are tabs 34 extending outwardly from rear waistband 32. In operation, tabs 34 will mate with corresponding patches 34' of hook and loop material, respectively, placed on the outside of front waistband 30 when the diaper 10 is worn by the baby to effectively connect rear waistband 32 to front waistband 30.

Snugging tabs 35 are provided on the outside of the flaps 16 of the rear portion 11 of the diaper 10 near leg indentations 18. These tabs 35, like tabs 34, are provided with hook and loop material adapted to mate with corresponding pads 37 of hook and loop material, respectively, on the outside of outer cover 14 adjacent fold lines 15 on the front portion 13 of the diaper 10. When the diaper 10 is placed on a baby, said tabs and pads 35 and 37, respectively, are brought into contact to further releasably connect the rear portion 11 to the front portion 13 of diaper 10 about the legs of a wearer.

Figure 2:
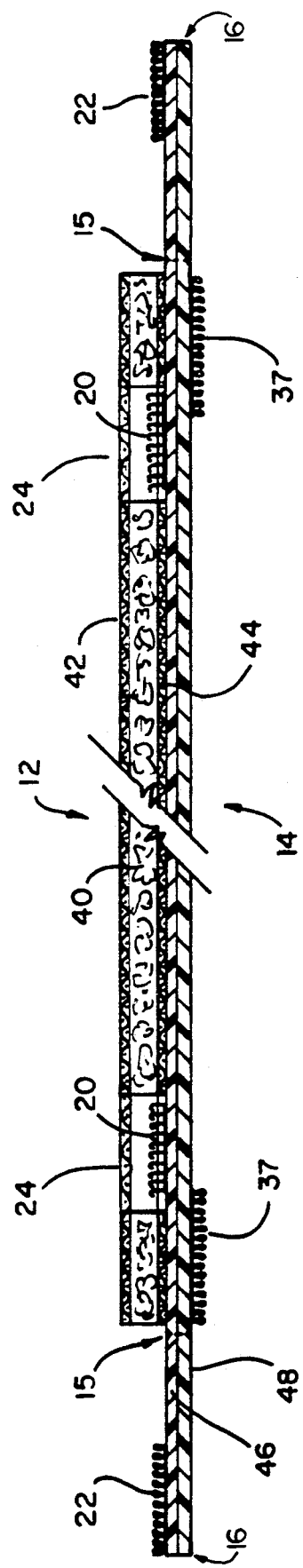
FIG. 2 shows a cross-sectional view of the invention along the line labeled 2 in FIG. 1 through the inner liner and outer cover with the inner liner in place above the outer cover as shown in FIG. 1.

As shown in FIG. 2, outer cover 14, shown in cross-sectional view, has a base layer 46 to which flaps 16 are integrally and hingedly attached along fold lines 15. In the preferred embodiment, flaps 16 and base 46 are formed of a continuous sheet of the same material, flaps 16 being differentiated from base 46 only by the presence of fold lines 15.

Inner liner 12 is removably connectable to outer cover 14 by way of connecting means, which, in the preferred embodiment, is comprised of male and female hook and loop fastener members 20 and 22 positioned on opposite sides of fold lines 15 so as to mate within corresponding apertures 24 defined by inner liner 12.

An outer layer or shell 48 may be attached to base 46 by any common means, and may be decorated with a decorative pattern if desired. Shell 48 may also be constructed of a material impervious to liquids.

Figure 3:
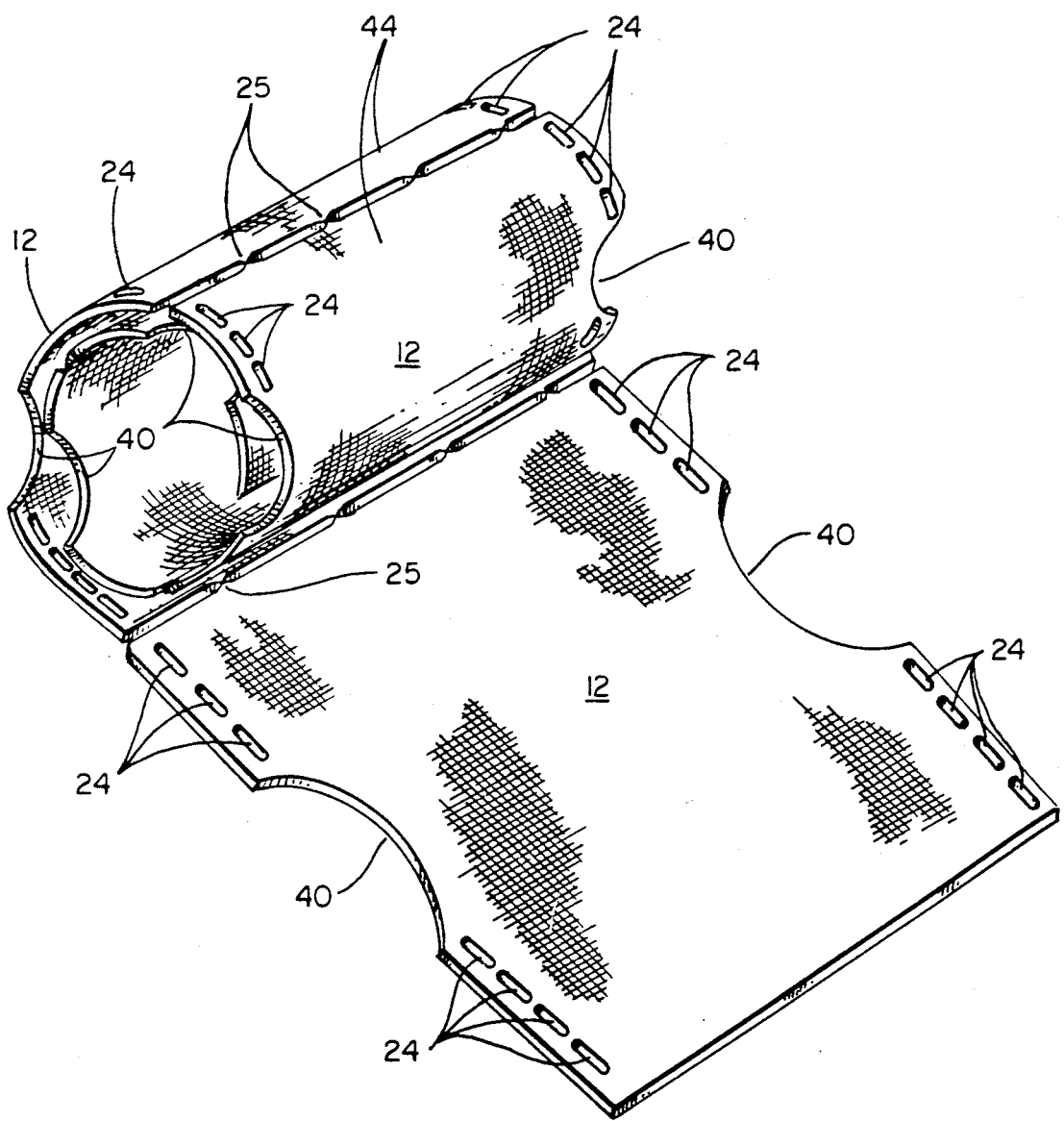
FIG. 3 is a perspective view of a plurality of inner liners attached sequentially along perforations.

A plurality of inner liners 12 may be connected together along perforations as shown in FIG. 3 so that a series of inner liners 12 may be placed on a roll such as is done with a roll of paper towels.

As shown in FIG. 1, inner liner 12 has a shape corresponding generally to outer cover 14. In particular, inner liner 12 has the shape of outer cover 14 below rear waistband 32, following fold line 15 to leg indentation 18, continuing on fold 15 to front waistband 30 and following a similar path on the opposite side.

After an inner liner 12 to be used is placed upon the body-facing surfaces of outer cover 14 and apertures 24 aligned with connecting members 20. Flaps 16 are then folded along fold lines 15 so that connecting members 22 come into mating contact with members 20 through apertures 24. The interaction of the hook and loop connectors of members 20 and 22 securely hold flaps 16 against inner liner 12 which in turn is held against outer cover 14. In this way, inner liner 12 is held securely in position relative to outer cover 14.

As mentioned above and as shown in FIG. 2, inner liner 12 is constructed of an absorbent material 40 covered with wick material 42, which in turn is supported by a liquid impervious layer 44 The wick material 42 draws contaminants away from the wearer's body and draws it toward the absorbent material 40. Liquid impervious layer 44 keeps within absorbent material 40. Inner liners 12 are adapted to be disposed at an appropriate time after use. In addition, inner liners 12 may be pre-sterilized and pre-powdered as desired to meet the individuals needs of the baby, and should be degradable so as to disintegrate as soon after use as possible.

Since the inner liner 12 is the only part of the diaper being disposed of after use, the amount of diaper material, and hence volume of waste, that is being disposed of is considerably less than that which is traditionally thrown away with a full disposable diaper. This reduction in significantly reduces the impact disposable diapers have on waste treatment facilities currently available, such as landfills.

After securely attaching inner liner 12 to outer cover 14, the diaper may be placed upon the baby. This is done in the traditional manner by seating the baby upon the rear portion 11 of the diaper 10. At this time the front portion 13 of the diaper is brought between the baby's legs. Then tabs 34 may be brought into contact with pads 34' on the front waistband 30. As mentioned, tabs 34 and pads 34' have corresponding connecting means so that when tabs 34 are brought into contact with pads 34' a strong effective seal is formed thereby effectively connecting front waistband 30 to rear waistband 32. Also, flaps 16 of the rear portion 11 of diaper 10 are brought into contact with the outer cover 12 along fold lines 15 of the front portion 13 of diaper 10. This allows connecting tabs 35 on the rear portion 11 of diaper 10 to mate with connecting pads 37 on the front portion 13 of diaper 10 as explained above to connect the edges around the leg indentation 18 of both the rear and front portions 11, 13 of the diaper 10.

This connection of front waistband 30 to rear waistband 32 and tabs 35 to pads 37 conforms the diaper 10 to the shape of the baby.

Although a hook and loop fastening system for the connections of this invention has been shown and described as a preferred embodiment, it is within the scope of this invention to provide any means for connecting such as buttons, snaps or the like.

In addition, although the preferred embodiment for inner liner 12 is that they be connected along perforations 50 in a roll, as shown in FIG. 3, inner liners 12 may also be provided in any other means such as individually boxed with or without connection to each other, or by any other means of presenting such liners.

While the invention has been described in connection with the particular embodiment, it is to be understood that this description has been by way of example and not for limitation. Additions and modifications may be made to the disclosure and still be within the scope of this invention. In addition, obvious changes and additions may be made by a person skilled in the art.

I claim:

1. A diaper comprising:
   a substantially hourglass-shaped outer cover having opposed elongated side edges and having flaps attached to said side edges along fold lines, means for releasably attaching said flaps to said outer cover when said flaps are folded along said fold lines; and
   an inner liner corresponding substantially in shape to said outer cover and defining apertures extending through said inner liner corresponding in position to said means for releasably attaching said flaps when said inner liner is superimposed upon said outer cover, so that said means for releasably attaching said flaps connects through said apertures thereby holding said inner liner in position relative to said outer cover.

2. The diaper of claim 1 wherein said means for releasably attaching said flaps to said outer cover comprises a hook and loop fastening system wherein said hooks are attached to either said flaps or said outer cover, which said hooks are adapted to be brought into contact with said loops attached to said outer cover or said flaps, respectively, to retain said inner liner in position relative to said outer cover.

3. The device of claim 2 wherein a plurality of said hooks are arranged along each of said folds and corresponding said loops are symmetrically arranged along said folds.

4. A diaper system comprising:
   a substantially hour-glass shaped outer cover having opposed elongated side edges and having flaps attached to said side edges along fold lines, said side edges each being interrupted by leg recesses, said diaper having means for releasably attaching said flaps to said outer cover when said flaps are folded along said fold lines; and
   a disposable insert means comprising an inner liner corresponding substantially in shape to said outer cover and defining apertures extending therethrough, said apertures corresponding in position to said means for releasably attaching said flaps to said outer cover such that said means for releasably are positioned to connect through said apertures thereby holding said inner liner in position relative to said outer cover, said inner liner being sequentially attached to a plurality of like inner liners by means for releasably attaching each of said inner liners to sequential other of said inner liners in a continuous sheet means for dispensing.

5. The insert means of claim 4 wherein said means for attaching one of said inner liners to sequential other of said inner liners is a tearable perforation.

6. The device of claim 1 wherein said inner liner includes a liquid absorbent layer.

7. The device of claim 6 wherein said inner liner includes a liquid impervious layer.

8. The device of claim 1 wherein said inner liner includes a layer impregnated with pulverant baby powder, said impregnated layer positioned adjacent a baby wearing said diaper.

9. The device of claim 1 wherein said outer cover includes a liquid impervious layer.

10. A diaper comprising:
    an outer cover, substantially hourglass shaped, said outer cover having flaps attached thereto along fold lines, said flaps and said outer cover having means for releasably attaching said flaps to said outer cover when folded along said fold lines, said flaps defining opposed leg recess means for receiving the legs of a wearer of said diaper, said means for releasably attaching said flaps to said outer cover comprising a hook and loop fastening system wherein said hooks are attached to either said flaps or said outer cover, which said hooks are brought into contact with said loops attached to said outer covering or said flaps, respectively, said outer cover including a liquid impervious layer; and,
    an inner liner corresponding substantially in shape to said outer cover and defining apertures extending through said inner liner corresponding in position to said means for releasably attaching said flaps when said inner liner is superimposed upon said outer cover, so that said means for releasably attaching said flaps connect through said through said apertures thereby holding said inner liner in position relative to said outer cover.

11. A diaper comprising:
    an outer cover, substantially hourglass shaped, said outer cover having elongated opposed side edges defining leg recess means, said outer cover further having flaps attached thereto along fold lines, said flaps and said outer cover having means for releasably attaching said flaps to said outer cover when folded along said fold lines, said means for releasably attaching said flaps to said outer cover comprising male connecting means integrally connected to said diaper along each of said fold lines and corresponding female connecting means integrally connected to said diaper symmetrically opposite said male connecting means relative to each of said fold lines, said male connecting means adapted to be brought into contact with said female connecting means when said flaps are folded about said fold lines; and
    an inner liner corresponding substantially in shape to said outer cover and defining apertures extending through said inner liner corresponding in position to said means for releasably attaching when said inner liner is superimposed upon said outer cover, so that said male connecting means and female connecting means may be brought into registry with said aperture and connected through said apertures thereby holding said inner liner in position relative to said outer cover.

12. The diaper of claim 11, wherein
    said inner liner also includes a liquid absorbent layer and a liquid impervious layer, said liquid impervious layer positioned adjacent said outer cover and said liquid absorbent layer positioned adjacent a wearer of said diaper.

* * * * *